United States Patent [19]

Kenyon

[11] Patent Number: 4,916,240
[45] Date of Patent: Apr. 10, 1990

[54] HETERO-POLYCYCLIC AROMATIC COMPOUNDS

[75] Inventor: Ronald W. Kenyon, Manchester, England

[73] Assignee: Imperial Chemical Industries PLC, London, England

[21] Appl. No.: 199,056

[22] Filed: May 26, 1988

[30] Foreign Application Priority Data

Jun. 1, 1987 [GB] United Kingdom ............... 8712784

[51] Int. Cl.$^4$ .......................................... C07D 491/04
[52] U.S. Cl. ..................................... 549/299; 549/45;
549/47; 549/60; 549/472; 548/431; 548/433;
548/526; 548/469; 546/270; 546/174; 8/636;
8/922
[58] Field of Search ................. 549/299, 60, 472;
546/270, 174, ; 548/526, 469

[56] References Cited

U.S. PATENT DOCUMENTS

| 4,115,404 | 9/1978 | Greenhalgh et al. | 549/299 |
| 4,650,882 | 3/1987 | Kenyon et al. | 549/299 |
| 4,680,417 | 7/1987 | Kenyon et al. | 549/299 |

OTHER PUBLICATIONS

Fueistenwerth CA 108:152148r.

*Primary Examiner*—Jane T. Fan
*Attorney, Agent, or Firm*—Cushman, Darby & Cushman

[57] ABSTRACT

Compounds of the general formula:

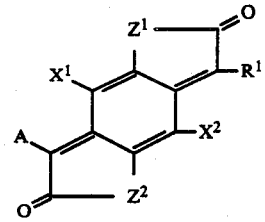

wherein
$Z^1$ and $Z^2$ are each independently —O—, —S— or —NR$^5$— in which R$^5$ is hydrogen, an optionally substituted hydrocarbon group or an acyl group;
$X^1$ and $X^2$ are selected from hydrogen, halogen, cyano, $C_{1-4}$ alkyl, $C_{1-4}$ alkoxy, aryl, carbamoyl, sulphamoyl, carboxy or carboxylic acid ester;
$R^1$ is an optionally substituted aryl radical;
A is an optionally substituted alkyl radical or a radical of the formula:

$$R^2-(CH=CH)_n-$$

in which
$R^2$ is an optionally substituted aryl or heterocyclic radical, and
n has a value of 1 or 2.

The compounds are useful as dyes for synthetic textile materials.

4 Claims, No Drawings

HETERO-POLYCYCLIC AROMATIC COMPOUNDS

This invention relates to hetero-polycyclic aromatic compounds, to a method for their preparation and to their use in the coloration of textile materials.

According to the invention, there are provided compounds of the general formula:

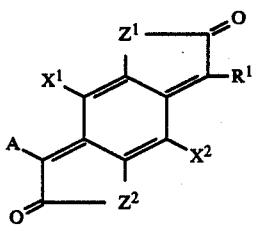   I wherein
$Z^1$ and $Z^2$ are each independently —O—, —S— or —NR$^5$— in which R$^5$ is hydrogen, an optionally substituted hydrocarbon group or an acyl group;
$X^1$ and $X^2$ are selected from hydrogen, halogen, cyano, $C_{1-2}$ alkyl, $C_{1-4}$ alkoxy, aryl, carbamoly, sulphamoyl, carboxy or carboxylic acid ester;
$R^1 X^2$ are selected from hydrogen, halogen, cyano, $C_{1-4}$ alkykl, $C_{1-4}$ alkoxy, aryl, carbamoyl, sulphamoyl, $R^1$ is an optionally substituted aryl radical;
A is an optionally substituted aryl radical or a radical of the formula:

   II in which
$R^2$ is an optionally substituted aryl or heterocyclic radical, and
n has a value of 1 or 2.

The optionally substituted hydrocarbon group represented by $R^5$ is preferably $C_{1-8}$-alkyl, and more preferably $C_{1-4}$-alkyl, or monocyclic aryl, more preferably phenyl which may be substituted by groups selected from hydroxy, halogen, nitro and alkoxy. Where $R^5$ is monocyclic aryl it may also be substituted by an alkyl and where $R^5$ is alkyl it may also be substituted. The acyl group represented by $R^5$ is preferably $C_{1-4}$-alkyl- or monocyclic arylcarbonyl or arylsulphonyl which may be substituted by one or more groups selected from hydroxy, halogen, nitro, $C_{1-4}$-alkyl and $C_{1-4}$-alkoxy. Examples of the optionally substituted hydrocarbon groups represented by $R^5$ are alkyl and preferably $C_{1-4}$-alkyl, such as methyl, ethyl, n-propyl and iso-propyl; substituted alkyl, preferably substituted $C_{1-4}$-alkyl, such as beta-hydroxyethyl, beta-methoxyethyl and beta-ethoxyethyl; phenyl and substituted phenyl such as tolyl, chlorophenyl, nitrophenyl and $C_{1-4}$-alkoxyphenyl. Examples of the acyl groups represented by $R^5$ are acetyl, propionyl, n-butyryl, benzoyl and m-nitrobenzoyl, p-chlorobenzoyl, p-methylbenzoyl, p-methoxybenzoyl and p-hydroxybenzoyl.

The aryl groups represented by $X^1$ and $X^2$ are preferably mono-homocyclic aryl, that is phenyl and substituted phenyl. The $C_{1-4}$-alkyl and alkoxy groups represented by $X^1$ and $X^2$ may also be substituted and examples of suitable substituents for these and the aryl groups are hydroxy, halogen, nitro, $C_{1-4}$-alkyl and $C_{1-4}$-alkoxy. The carbamoyl and sulphamoyl groups represented by $X^1$ and $X^2$ are preferably of the formula—$CONL^1L^2$ or—$SO_2NL^1L^2$ wherein $L^1$ and $L^2$ are each independently hydrogen, $C_{1-4}$-alkyl or monocyclic aryl, preferably phenyl. The carboxylic acid ester groups represented by $X^1$ and $X^2$ are preferably of the formula—$COOL^3$ wherein $L^3$ is optionally substituted alkyl, especially $C_{1-4}$-alkyl, or monocyclic aryl, especially phenyl.

Optionally substituted aryl radicals represented by $R^1$ include naphthyl and, preferably, optionally substituted phenyl radicals. Substituents which may be present on phenyl radicals include halogen, hydroxy, alkoxy, for example $C_{1-4}$-alkoxy, alkenyloxy, for example $C_{2-4}$-alkenyloxy, alkyl, for example $C_{1-4}$-alkyl, alkylthio, for example $C_{1-4}$-alkylthio, thiol, acylamino, primary, secondary or tertiary amino, acyloxy and substituted alkoxy, for example aralkyloxy and groups of the formulae:

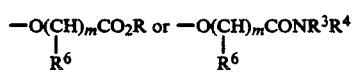

wherein m has a value of 1–4, R, $R^3$ and $R^4$ are hydrocarbon, especially alkyl or aryl radicals, and $R^6$ is hydrogen or lower alkyl.

Optionally substituted alkyl which may be represented by A are preferably $C_{1-8}$, and more preferably $C_{1-4}$ alkyl, especially methyl, radicals.

Optionally substituted aryl radicals which may be represented by $R^2$ include naphthyl, anthryl, phenanthryl, pyrenyl, fluorenyl and, preferably, optionally substituted phenyl radicals. Substituents which may be present on phenyl radicals include alkyl, for example $C_{1-4}$-alkyl, alkoxy, for example $C_{1-4}$-alkoxy, alkenyloxy, for example $C_{2-4}$-alkenyloxy, aryloxy, aralkyloxy, aryl, halogen, primary, secondary or tertiary amino, acylamino, acyloxy, cyano, hydroxy, carboxylic ester, carbamoyl, alkylthio, nitro, styryl, trifluoromsthyl, alkenyl and substituted alkoxy, for example groups of the formulae:

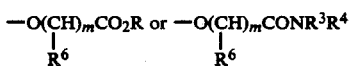

as defined above.

Heterocyclic radicals which may represented by $R^2$ include furyl, pyrrolyl, thienyl, indolyl, pyridyl and quinolyl radicals.

Preferred structures of Formula I, for use as dyes, have at least one of the following characteristics:
$X^1$ and $X^2$ are both hydrogen;
(ii) $Z^1$ and $Z^2$ are both oxygen, and
(iii) A is a group of Formula II in which n is 1.

The compounds of Formula I in which A is an optionally substituted alkyl radical may be prepared by reacting an alpha-ketoacid of the formula:

   III wherein $R^7$ is optionally substituted alkyl with a compound of the formula:

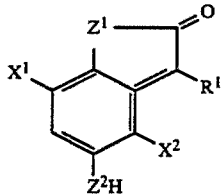

wherein $R^1$, $X^1$, $X^2$, $Z^1$ and $Z^2$ have the meanings given above, in the presence of strong sulphuric acid or methanesulphonic acid.

The compounds of Formula I in which A is a radical of Formula II may be prepared by reacting a compound of the formula:

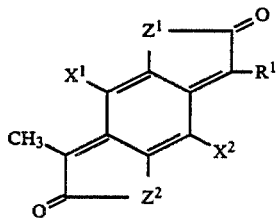

(obtained by reacting a compound of Formula IV with pyruvic acid) with an aldehyde of the formula:

$$R^2-(CH=CH)_{n-1}CHO \qquad VI$$

wherein $R^1$, $R^2$, $X^1$, $X^2$, $Z^1$, $Z^2$ and n have the meanings given above.

The reaction between the compounds of Formula V and Formula VI may conveniently be performed in an inert solvent, for example toluene, xylene or chlorobenzene in the presence of a catalyst, for example a mixture of acetic acid and piperidine at a temperature in the range of from 50° to reflux temperature.

The compounds of Formula I are suitable for the coloration of synthetic textile materials, especially polyesters, giving yellow to greenish blue shades. They have high extinction coefficients in the region of 400 to 700 nm and generally build-up well on the textile material to give strong shades, the compounds in which A is a group of Formula II being tinctorially stronger than the corresponding diaryl benzodifuranones. They have good light fastness and very good wet and heat fastness properties. They are generally suitable for application as aqueous dispersions by recognized dyeing and printing techniques for aromatic polyester textile materials.

The invention is further illustrated by the following Examples in which all parts and percentages are by weight unless otherwise indicated.

EXAMPLE 1

A mixture of 1.12 g of 3-methyl-7-phenyl-2,6-dioxo-2,6-dihydrobenzo[1:2-b, 4:5-b']difuran. 1.0 g of benzaldehyde, 20 ml of chlorobenzene and 0.1 g of a mixture of acetic acid and piperidine in the ratio 5:1, is stirred and heated at 125°-130° C. for 75 minutes. The mixture was then cooled to 25° C. and the product, 3-styryl-7-phenyl-2,6-dioxo-2,6-dihydrobenzo[1:2-b, 4:5-b']difuran, filtered off, washed with methanol and dried. The product dissolves in chloroform to give a red solution having an absorption maximum at 508 nm and the mass spectrum shows a molecular ion at 366. When applied to polyester textile materials, it gives bright red shades with good heat fastness and excellent wet fastness.

The 3-methyl-7-phenyl-2,6-dioxo-2,6-dihydrobenzo[1:2-b, 4:5-b']difuran used in this Example was prepared by stirring a mixture of 45.2 g of 5-hydroxy-2-oxo-3-phenyl-2:3-dihydrobenzofuran, 20 g of pyruvic acid and 500 ml of 80% sulphuric acid at 70-80° C. for 18 hours. The mixture was then cooled to 25° C. and added to 400 g of stirred ice water and the precipitated product filtered off, washed acid free with water and then washed with methanol and dried. The product dissolves in chloroform to give a bright yellow solution having an absorption maximum at 422 nm. The mass spectrum showed an intense molecular ion at 278.

It gave bright yellow shades when padded onto polyester and baked at 180° C. for 2 minutes.

EXAMPLE 2

In place of the 1.0 g of benzaldehyde used in Example 1, there was used 0.7 g of m-tolualdehyde. The product, 3-[3-methylstyryl]-7-phenyl-2,6-dioxo-2,6-dihydrobenzo[1:2-b, 4:5-b']difuran, dissolves in chloroform to give a red solution having an absorption maximum at 512 nm. When applied to polyester textile materials, it gives bright bluish-red shades having good fastness properties and good build-up.

EXAMPEL 3

In place of the 1.12 g of 3-methyl-7-phenyl-2,6-dioxo-2,6-dihydrobenzo[1:2-b, 4:5-b']difuran used in Example 1, there was used 1.17 g of 3-methyl-7-[4-methylphenyl]-2,6-dioxo-2,6-dihydrobenzo[1:2-b, 4:5-b']difuran. The product, 3-styryl-7[4-methylphenyl]-2,6-dioxo-2,6-dihydrobenzo[1:2-b, 4:5-b']difuran, dissolves in chloroform to give a bluish-red solution having an absorption maximum at 518 nm. When applied to polyester textile materials, it gives bright bluish-red shades having good fastness properties.

The 3-methyl-7-[4-methylpheny]-2,6-dioxo-2,6-dihydrobenzo[1:2-b, 4:5-b']difuran was prepared by stirring a mixture of 4.8 g of 5-hydroxy-2-oxo-3-(4-methylphenyl)-2:3-dihydrobenzofuran, 1.8 g of pyruvic acid and 40 g of methane sulphuric acid at room temperature for 18 hours. The mixture was added to 400 g of ice water and the product filtered off, washed acid free with water and then with methanol and dried. It dissolves in chloroform to give a yellow solution having an absorption maximum at 432 nm. When applied to polyester textile materials, it gives reddish-yellow shades.

EXAMPLE 4

In place of the 1.0 g of benzaldehyde used in Example 1, there is used 1.5 g of 4-n-butylbenzaldehyde. The product, 3-[4-n-butylstyryl]-7-phenyl-2,6-dioxo-2,6-dihydrobenzo[1:2-b, 4,5-b']difuran, dissolves in chloroform to give a bluish-red solution having an absorption maximum at 522 nm. When applied to polyester textile materials, it gives bright bluish-red shades with good fastness properties.

EXAMPLE 5

In place of the 1.0 g of benzaldehyde used in Example 1, there is used 1.5 g of 4-isopropylbenzaldehyde. The product, 3-[4-isopropylstyryl]-7-phenyl-2,6-dioxo-2,6-dihydrobenzo[1:2-b, 4,5-b']difuran, dissolves in chloroform to give a bluish-red solution having an absorption maximum at 520 nm. When applied to polyester textile materials, it gives bright bluish-red ades with good fastness properties.

EXAMPLE 6

In place of the 1.0 g of benzaldehyde used in Example 1, there is used 1g of p-tolualdehyde. The product, 3-[4-methylstyryl]-7-phenyl-2,6-dioxo-2,6-dihydrobenzo[1:2-b, 4,5-b']difuran, dissolves in chloroform to give a bluish-red solution having an absorption maximum at 518 nm. When applied to polyester textile materials, it gives bright bluish-red shades with good fastness properties.

EXAMPLE 7

In place of the 1.0 g to benzaldehyde used in Example 1, there is used 1.15 g of m-hydroxybenzaldehyde. The product, 3-(3-hydroxystyryl)-7-phenyl-2,6-dioxo-2,6-dihydrobenzo[1:2-b, 4,5-b']difuran, dissolves in chloroform to give a bluish-red solution having an absorption maximum at 512 nm. When applied to polyester textile materials, it gives bright bluish-red shades with good fastness properties.

EXAMPLE 8

In place of the 1.0 g of benzaldehyde used in Example 1, there is used 1.0 g of m-chlorobenzaldehyde. The product, 3-[3-chlorostyryl]-7-phenyl-2,6-dioxo-2,6-dihydrobenzo[1:2-b, 4,5-b']difuran, dissolves in chloroform to give a red solution having an absorption maximum at 505 nm. When applied to polyester textile materials, it gives bright yellowish-red shades with good fastness properties.

EXAMPLE 9

In place of the 1.0 g of benzaldehyde used in Example 1, there is used 1.0 g of m-methoxybenzaldehyde. The product, 3-[3-methoxystyryl]-7-phenyl-2,6-dioxo-2,6-dihydrobenzo1:2-b, 4,5-b']difuran, dissolves in chloroform to give a red solution having an absorption maximum at 513 nm. When applied to polyester textile materials, it gives bright bluish-red shades having good build up and good fastness properties.

EXAMPLE 10

In place of the 1.12 g of 3-methyl-7-phenyl-2,6-dioxo2,6-dihydrobenzo[1:2-b, 4:5-b']difuran used in Example 1, there is used 1.17 g of 3-methyl-7-[3-methylphenyl]-2,6-dioxo-2,6-dihydrobenzo[1:2-b, 4:5-b']difuran. The product, 3-styryl-7[3methylphenyl]-2,6-dioxo-2,6-dihydrobenzo[1:2-b, 4:5-b']difuran, dissolves in chloroform to give a red solution having an absorption maximum at 510 nm. When applied to polyester textile materials, it gives bright red shades having good build up and good fastness properties.

The 3-methyl-7-[3-methylpheny]-2,6-dioxo-2,6-dihydrobenzo[1:2-b, 4:5-b']difuran used in this Example can be prepared by stirring a mixture of 24 g of 5-hydroxy-2-oxo-3-(3-methyl- phenyl)-2:3-dihydrobenzofuran, 10 g of pyruvic acid and 250ml of 80% sulphuric acid at 70°-80° C. for 18 hours. After cooling, the mixture was added to 1000 g of ice water and the product filtered off, washed acid free with water and then with methanol and dried. It dissolves in chloroform to give a yellow solution having an absorption maximum at 423 nm.

EXAMPLE 11

In place of the 1.0 g of benzaldehyde used in Example 10, there is used 1.0 g of methoxybenzaldehyde. The product, 3-[3-methoxystyryl]-7-[3-methylphenyl]-2,6-dioxo-2,6-dihydrobenzo[1:2-b, 4,5-b']difuran, dissolves in chloroform to give a red solution having an absorption maximum at 513 nm. When applied to polyester textile materials, it gives bright bluish-red shades having good build up and good fastness properties.

EXAMPLE 12

In place of the 1.0 g of benzaldehyde used in Example 10, there is used 1.0 g of m-tolualdehyde. The product, 3-[3-methylstyryl]-7-[3-methylphenyl]-2,6-dioxo-2,6-dihydrobenzo[1:2-b, 4.5-b']difuran, dissolves in chloroform to give a red solution having an absorption maximum at 514 nm. When applied to polyester textile materials, it gives bright bluish-red shades having good build up and good fastness properties.

EXAMPLE 13

In place of the 1.0 g of benzaldehyde used in Example 1, there is used 2.0 g of 3-formylphenoxyacetic acid. The product, 3-[3-carboxymethoxystyryl]-7-phenyl-2,6-dioxo-2,6-dihydrobenzo[1:2-b, 4:5-b']difuran was then esterified by adding 0.66 g to 20 ml of methyl cellosolve and 0.5 g of concentrated sulphuric acid and heating at 100° C. for 1 hour. After cooling, the product, 3-[3-methoxyethoxycarbonylmethoxystyryl]-7-phenyl-2,6-dioxo-2.6-dihydrobenzo[1:2-b, 4:5-b']difuran, was filtered off, washed with methyl cellosolve and then with methanol and dried.

It dissolves in chloroform to give a red solution having an absorption maximum at 510 nm. When applied to polyester textile materials, it gives bright red shades having good build up and good fastness properties.

EXAMPLE 14

In place of the 2.0 g of 3-formylphenoxyacetic acid used in Example 13, there is used 1.5 g of methyl-3-formylphenoxyacetate. The product, 3-[3-methoxycarbonylmethoxystyryl]-7-phenyl2,6-dioxo-2,6-dihydrobenzo[1:2-b, 4:5-b']difuran, dissolves in chloroform to give a red solution having an absorption maximum at 508 nm. When applied to polyester textile materials, it gives bright red shades having good fastness properties.

EXAMPLE 15

0.5 g of 3-[3-methoxycarbonylmethoxystyryl]-7-pnenyl-2,6-dioxo-2,6-dihydrobenzo[1:2-b, 4:5-b']difuran obtained as in Example 14 was added to a mixture of 20 g of methyl cellosolve and 0.5 g of concentrated sulphuric acid and heated at 130°-140° C. for 3 hours. On cooling, the product crystallised and was filtered off and dried and was identical to that obtained in Example 13.

In place of the 3-methyl-7-phenyl-2,6-dioxo-2,6-dihydrobenzo-[1:2-b, 4:5-b']difuran used in Example 14, there is used 1.17 g of 3-methyl-7(3-methylphenyl)-2,6-dioxo-2,6-dihydrobenzo[1:2-b, 4:5-b']difuran. To 0.5 g of the product, 3-[3-methoxycarbonylmethoxystyryl]-7-(3-methylphenyl)-2,6-dioxo-2,6-dihydrobenzo[1:2-b, 4:5-b']difuran, was added a mixture of 20 g of methyl cellosolve and 0.5 g of concentrated sulphuric acid and the mixture stirred at 140°-140° C. for 1½hours. On cooling, the product, 3-[3-methoxyethoxycarbonylmethoxystyryl]-7-(3-methylphenyl)-2,6-dioxo-2,6-dihydrobenzo[1:2-b, 4:5-b']difuran, was filtered off and dried. It dissolves in chloroform to give a red solution having an absorption maximum at 512 nm. On application to polyester textile materials, it gives bright red shades showing good fastness properties.

EXAMPLE 17

In place of the 1.0 g of benzaldehyde used in Example 10, there is used 1.0 g of o-tolualdehyde. The product, 3-(2-methylstyryl)-7-(3-methylphenyl)-2,6-dioxo-2,6-dihydrobenzo[1:2-b, 4,5-b']difuran, dissolves in chloroform to give a red solution having an absorption maximum at 515 nm. When applied to polyester textile materials, it gives bluish-red shades having good fastness properties.

EXAMPLE 18

In place of the 1.0 g of benzaldehyde used in Example 1, there is used 1.5 g of furan-2-aldehyde. The product, 3-[2-furanylvinyl]-7-phenyl)-2,6-dioxo-2,6-dihydrobenzo[1:2-b, 4,5-b']difuran, dissolves in chloroform to give a reddish-violet solution having an absorption maximum at 543 nm. When applied to polyester textile materials, it gives reddish-violet shades with good build up.

EXAMPLE 19

In place of the 1.0 g of benzaldehyde used in Example 1, there is used 1.5 g of thiophene-2-aldehyde. The product, 3-[2-thienylvinyl]-7-phenyl)-2,6-dioxo-2,6-dihydrobenzo[1:2-b, 4,5-b']difuran, dissolves in chloroform to give a reddish-violet solution having an absorption maximum at 534 nm. When applied to polyester textile materials, it gives reddish-violet shades with good build up.

EXAMPLE 20

1.0 g of 3-(3-hydroxystyryl)-7-phenyl)-2,6-dioxo-2,6-dihydrobenzo- [1:2-b, 4,5-b']difuran, prepared as in Example 7, was added to a mixture of 20ml of pyridine and 2 ml of acetic anhydride. The mixture was stirred and heated at 80°-90° C. for 2 hours and then cooled to room temperature. The product, 3-(3-acetoxystyryl)-7-phenyl-2,6-dioxo-2,6-dihydrobenzo[1:2-b, 4:5-b']difuran, was filtered off, washed with methanol and then with water and dried. It dissolves in chloroform to give a red solution having an absorption maximum at 506 nm. When applied to polyester textile materials, it gives bright red shades with good fastness properties.

EXAMPLE 21

In place of the 1.0 g of benzaldehyde used in Example 1, there was used 1.5 g of p-chlorobenzaldehyde. The product, 3-(4-chlorostyryl)-7-phenyl-2,6-dioxo-2,6-dihydrobenzo[1:2-b, 4:5-b']difuran, dissolves in chloroform to give a red solution having an absorption maximum at 512 nm. When applied to polyester textile materials, it gives bright bluish-red shades with good fastness properties.

EXAMPLE 22

A mixture of 0.85 g of 3-methyl-7-(4-beta-ethoxyethoxy- carbonylmethoxyphenyl)-2,6-dioxo-2,6-dihydrobenzo[1:2-b, 4:5-b']difuran, 0.8 g of m-tolualdehyde, 15 ml of chlorobenzene and 0.1 g of a mixture of acetic acid and piperidine in the ratio 1:2 was stirred and heated under reflux for 40 minutes. The mixture was then cooled and the product, 3-(3-methylstyryl)-7-(4-beta-ethoxyethoxy- carbonylmethoxyphenyl)-2,6-dioxo-2,6-dihydrobenzo[1:2-b, 4:5-b']difuran, filtered off, washed with chlorobenzene and then with methanol and dried. It dissolves in chloroform to give a bluish-red solution having an absorption maximum at 520 nm. When applied to polyester textile materials, it gives bright bluish-red shades having good build up and good fastness properties.

The 3-methyl-7-(4-beta-ethoxyethoxycarbonylmethoxyphenyl)-2,6-dioxo-2,6-dihydrobenzo[1:2-b, 4:5-b']difuran used in this Example was prepared by stirring a mixture of 10 g of 5-hydroxy-2-oxo-3-(4-carboxymethoxyphenyl)-2,3-dihydrobenzofuran, 3.5 g of pyruric acid and 100 ml of 73% sulphuric acid at 70°-75° C. for 18 hours. The mixture was then cooled to 25° C. and added to 800 g of ice water and the precipitated product filtered off and washed acid free with water and dried. 10.9 g of this product was added to 150 ml of 2-ethoxyethanol and 1ml of concentrated sulphuric acid and the mixture stirred under reflux for 6 hours. After cooling, the product was filtered off, washed with a little 2-ethoxyethanol and dried.

The 5-hydroxy-2-oxo-3-(4-carboxymethoxyphenyl)-2,3-dihydrobenzofuran was prepared by stirring a mixture of 5.5 g of hydroquinone, 11.3 g of 4-carboxymethoxandelic acid and 30 ml of 73% sulphuric acid and heating at 50°-60° C. for 4 hours. After cooling, the mixture was added to 300 g of ice water and the product filtered off, washed acid free with water and dried.

EXAMPLE 23

In place of the 1.0 g of benzaldehyde used in Example 1, there was used 1.5 g of 4-ethoxy-1-naphthaldehyde. The product, 3-(4-ethoxy-1-naphthylvinyl)-7-phenyl-2,6-dioxo-2,6-dihydrobenzo[1:2-b, 4:5-b']difuran, dissolves in chloroform to give a blue solution having an absorption maximum at 620 nm. When applied to polyester textile materials, it gives blue shades.

EXAMPLE 24

In place of the 1.0 g of benzaldehyde used in Example 1, there was used 1.5 g of 3-phenoxybenzaldehyde. The product, 3-(3-phenoxystyryl)-7-phenyl-2,6-dioxo-2,6-dihydrobenzo[1:2-b, 4:5-b']difuran, dissolves in chloroform to give a red solution having an absorption maximum at 508 nm. When applied to polyester textile materials, it gives bright red shades having good fastness properties.

EXAMPLE 25

In place of the 1.0 g of benzaldehyde used in Example 1, there was used 1.5 g of m-benzyloxybenzaldehyde. The product, 3-(3-benzyloxystyryl)-7-phenyl-2,6-dioxo-2,6-dihydrobenzo[1:2-b, 4:5-b']difuran, dissolves in chloroform to give a red solution having an absorption maximum at 510 nm. When applied to polyester textile materials, it gives bright bluish-red shades having good fastness properties.

EXAMPLE 26

In place of the 1.0 g of benzaldehyde used in Example 1, there was used 1.0 g of m-fluorobenzaldehyde. The product, 3-(3-fluorostyryl)-7-phenyl-2,6-dioxo-2,6-dihydrobenzo[1:2-b, 4:5-b']difuran, dissolves in chloroform to give a red solution having an absorption maximum at 500 nm. When applied to Polyester textile materials, it gives bright yellowish-red shades having good fastness properties.

EXAMPLE 27

In place of the 1.0 g of benzaldehyde used in Example 1, there was used 1.8 g of 2-methyl-4-(bis-beta-chloroethyl)aminobenzaldehyde. The product, 3-(2-methyl-4-(bis-beta-chloroethyl)- amminostyryl)-7-phenyl-2,6-dioxo-2,6-dihydrobenzo[1:2-b, 4:5-b']difuran, dissolves in chloroform to give a greenish-blue solution having an absorption maximum at 648 nm. When applied to polyester textile materials, it gives greenish-blue shades.

EXAMPLE 28

A mixture of 2.84 g of 5-hydroxy-2-oxo-3-(4-n-propoxy- phenyl)-2,3-dihydrobenzofuran, 0.9 g pyruvic acid, 50 ml toluene and 1.9 g p-toluene sulphonic acid was stirred and heated under reflux for 3 hours. It was then cooled to 20° C. and 100 ml of methanol added. The product, 3-methyl-7-(4-n-propoxyphenyl)-2,6-dioxo-2,6-dihydrobenzo[1:2-b, 4:5-b']difuran, was filtered off, washed with methanol and dried.

It can be purified by chromatography on a silica column eluting with toluene. It dissolves in chloroform to give an orange solution having an absorption maximum at 469 nm. When applied to polyester textile materials, it gives orange shades with good fastness properties.

EXAMPLE 29

A mixture of 1.0 g of 3-methyl-7(4-n-propoxyphenyl)2,6-dioxo-2,6-dihydrobenzo[1:2-b, 4:5-b']difuran, 1.0 g of m-tolualdehyde, 20 ml of chlorobenzene and 0.1 g of a mixture of acetic acid and piperidine in the ratio 2:1, is stirred and heated at 25°-130° C. for 30 minutes. The mixture was cooled to 20° C. and the product, 3-(3-methylstyryl)-7-(4-n-propoxyphenyl)-2,6-dioxo-2,6-dihydrobenzo[1:2-b, 4:5-b']difuran, filtered off, washed with a little chlorobenzene and then methanol and dried. It dissolves in chloroform to give a bluish-red solution having an absorption maximum at 553 nm. When applied to polyester textile materials, it gives bright bluish-red shades with good fastness properties.

I claim:
1. A compound of the formula:

wherein
$X^1$ and $X^2$ are selected from hydrogen, halogen, cyano, $C_{1-4}$-alkyl, $C_{1-4}$-alkoxy, phenyl, $—CONL^1L^2$, $—SO_2NL^1L^2$, $—COOL^3$ and substituted $C_{1-4}$-alkyl, $C_{1-4}$-alkoxy and phenyl in which the substitutents are selected from hydroxy, halogen, nitro, $C_{1-4}$-alkyl and $C_{1-4}$-alkoxy;
$L^1$, $L^2$ and $L^3$ are selected from hydrogen, $C_{1-4}$-alkyl and phenyl;
$R^1$ is selected from naphthyl, phenyl and substituted phenyl in which the substituents are selected from halogen, hydroxy, $C_{1-4}$-alkoxy, $C_{2-4}$-alkenyloxy, $C_{1-4}$alkylthio, thiol, and primary amino;
A is selected from $C_{1-8}$-alkyl and radicals of the formula:

$$R^2—(CH=CH)_n—$$

wherein $R^2$ is selected from naphthyl, anthryl, phenathryl, pyrenyl, fluorenyl, fluryl, pyrrolyl, thienyl, indolyl, pyridyl, quinolyl, phenyl and substituted phenyl in which the substituents are selected from $C_{1-4}$-alkyl, $C_{1-4}$-alkoxy, $C_{2-4}$-alkenyloxy, halogen, primary amino, cyano, hydroxy, carbamoyl, nitro, styryl, trifluoromethyl, carboxymethoxy and methoxycarbonylmethoxy, and n has a value of 1 or 2.

2. A compound according to claim 1 wherein both of $X^1$ and $X^2$ are hydrogen.

3. A compound according to claim 1 wherein A is a group of the formula:

$$R^2—CH=CH—$$

wherein
$R^2$ has the meaning given in claim 1.

4. A compound according to claim 1, said compound being 3-styryl-7-phenyl-2,6-dioxo-2,6-dihydrobenzo[1:2-b,4:5-b']difuran.

* * * * *